United States Patent [19]

Carlisle

[11] Patent Number: 4,532,938

[45] Date of Patent: Aug. 6, 1985

[54] ELECTROTHERAPY APPARATUS

[75] Inventor: Floyd L. Carlisle, Clinton, Conn.

[73] Assignee: Theratronics, Inc., Essex, Conn.

[21] Appl. No.: 491,607

[22] Filed: May 4, 1983

[51] Int. Cl.³ .......................... A61N 1/04; A61N 1/36
[52] U.S. Cl. ..................................... 128/801; 128/421
[58] Field of Search ................ 128/783, 791–793, 128/800–803, 419 R, 421–423, 24.1–24.5

[56] References Cited

U.S. PATENT DOCUMENTS

| 3,163,166 | 12/1964 | Brant et al. | 128/803 |
| 3,373,747 | 3/1968 | Tapper | 128/422 |
| 3,472,233 | 10/1969 | Sarbacher | 128/783 |
| 3,602,229 | 8/1971 | Jaros et al. | 128/421 |
| 4,033,356 | 7/1977 | Hara | 128/801 |
| 4,095,601 | 6/1978 | Aufranc | 128/422 |
| 4,121,594 | 10/1978 | Miller et al. | 128/422 |
| 4,124,028 | 11/1978 | Gallo | 128/422 |

FOREIGN PATENT DOCUMENTS

| 2900485 | 7/1980 | Fed. Rep. of Germany | 128/800 |
| 2267119 | 11/1975 | France | 128/422 |

Primary Examiner—Lee S. Cohen

[57] ABSTRACT

Self-contained hand held apparatus for causing controlled muscle contractions comprises a signal generator and cooperating holder, the holder bearing the electrodes by which the muscle stimulation pulses provided by the signal generator are delivered to a subject. The signal generator includes an electrical connector which is complementary to a connector integral with the holder whereby insertion of the signal generator into the holder establishes electrical connection between the pulse source and the electrodes.

4 Claims, 3 Drawing Figures

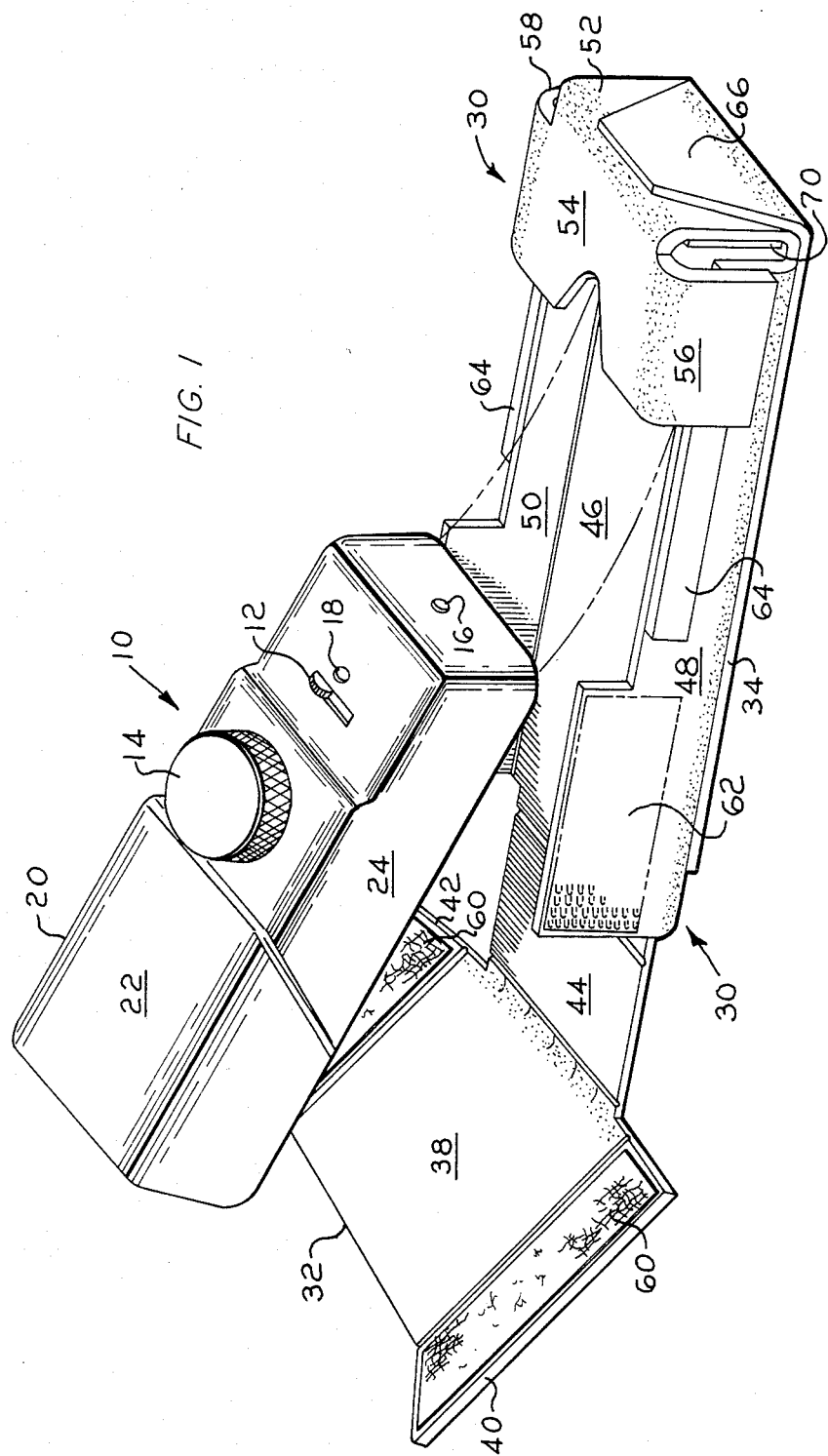

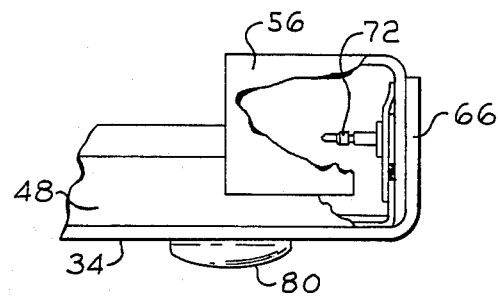
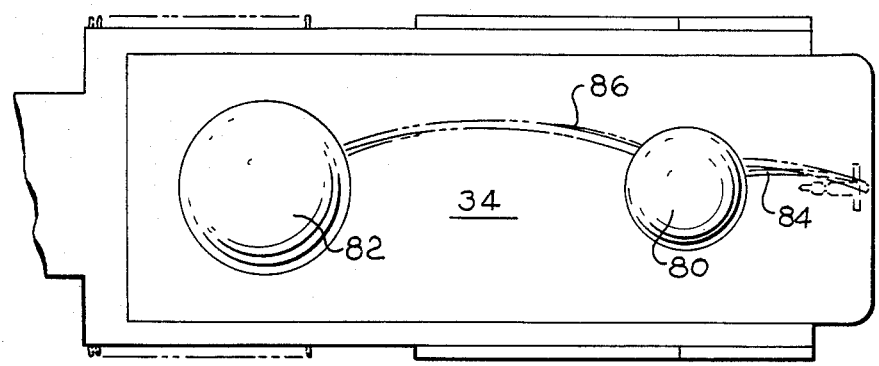

ELECTROTHERAPY APPARATUS

BACKGROUND OF THE INVENTION:

(1) Field of the Invention

The present invention relates to electrotherapy and particularly to the electrical stimulation of controlled muscle activity. More specifically, this invention is directed to massage devices which may be employed to cause controlled muscle contractions. Accordingly, the general objects of the present invention are to provide novel and improved methods and apparatus of such character.

(2) Description of the Prior Art

As employed herein the term "electrotherapy" relates to the direct application of electrical impulses to a living organism in the interest of achieving a therapeutic effect. As a science, electrotherapy has been know for many years. Apparatus employed for electrotherapy may be generally classified as nerve stimulators, which are generally intended to apply signals which interfere with the transmission of the sensation of pain to the brain, and muscle stimulators which are designed to cause controlled muscle contractions. In either case the object of electrotherapy is to stimulate the natural hearing and pain relief systems of the body when such systems are not functioning properly due to injury such as strains, sprains and bruises. In the case of muscle stimulation, the controlled contractions which are produced by the apparatus result in an increase in the flow of blood to and away from the damaged cells by alternately compressing and releasing the veins throughout the damaged area. This, of course, is what is accomplished by the alternate application of heat and cold and by massage, either manually or with apparatus such as an ultrasound transducer. The application of heat and cold is a very slow process whereas the various techniques for massage which are available generally require a great deal of expertise, particularly if the injury is not to be aggravated.

Examples of prior art electrical muscle stimulators may be seen in U.S. Pat. Nos. 2,641,259, 3,077,884, 4,114,893, 4,240,437, and 4,342,317. These examples of the prior art show the evolution of the apparatus which has been incident to the availability of solid state electronics, i.e., electrical muscle stimulators are rapidly becoming comparatively sophisticated devices considering the circuitry employed therein. However, as particularly evident from U.S. Pat. Nos. 4,144,893 and 4,240,437, the applicator portions of the devices have failed to evolve as rapidly as the electronics. Thus, in the prior art it is common to attach electrodes to the subject by means of belts or straps. This is often quite difficult to accomplish in the case of a four-legged animal. The need to use a belt or strap also impedes the ability to treat the subject in only a localized area. In many cases a single strapped-on electrode was used in conjuction with a hand-held applicator in the form of a rather cumbersome roller or the like which was inconveniently attached by a cable to a bulky combination signal generator and associated power supply.

SUMMARY OF THE INVENTION

The present invention overcomes the above briefly discussed and other deficiencies and disadvantages of the prior art by providing a novel and improved applicator which may be employed for the electrical stimulation of muscular activity. An applicator in accordance with the present invention is a self-contained device which is characterized by compactness and ease of use.

In accordance with the preferred embodiment, the invention comprises a control unit which includes all of the electronics required to produce the requisite electrical signals for causing the desired mode of muscle stimulation. The invention also includes a conveniently shaped carrying case into which the control unit may be easily inserted. The carrying case has, mounted thereon, a pair of spacially displaced electrodes. Insertion of the control unit into the carrying case automatically establishes communication between the signal generator and electrodes. The entire assembly of control unit and carrying case is sufficiently light-weight and compact to be held in the users hand whereby the desired body area may be contacted by the spaced electrodes and subsequently massaged while contact between the electrodes and the skin is maintained. The carrying case is designed such that the controls for varying the output frequency and/or intensity of the generated electrical signals, as well as the switch for activating the unit, are readily accessible.

BRIEF DESCRIPTION OF THE DRAWING

The present invention may be better understood and its numerous objects and advantages will become apparent to those skilled in the art by reference to the accompanying drawing wherein like reference numerals refer to like elements in the figures and wherein:

FIG. 1 is an exploded perspective view of a muscle stimulator in accordance with a first embodiment of the present invention, FIG. 1 depicting the control unit and carrying case.

FIG. 2 is a view of the carrying case of FIG. 1, taken from below, depicting the electrodes; and FIG. 3 is a partial side-elevational view, partly in section, of the carrying case of FIG. 2.

DESCRIPTION OF THE DISCLOSED EMBODIMENT

With reference to the drawing, a control unit is indicated generally at 10. Control unit 10 will include a power source, namely a battery, and the requisite circuitry for converting the DC current supplied by the battery into output pulses having the desired repetition rate, duration, magnitude, polarity and shape. In the disclosed embodiment, this circuitry will be coupled to the battery by means of an on/off switch which is coupled to an intensity control, in the form of a potentiometer, having a control knob 14. The initial rotation of knob 14 will close the switch to connect the battery to the oscillator, whereby pulse generation is initiated, and further rotation of knob 14 will vary the magnitude of the output pulses provided by the pulse generator. These output pulses are applied between the two terminals or contacts of a socket 16. A slide switch 12 will be employed to switch capacitors and/or resistors in the pulse generator circuit to permit selection of two or more pulse repetition rates. The control unit 10 may also be provided with a window 18 through which a pilot light, indicating the operative state of the device, may be observed.

In the disclosed embodiment the outer housing 20 of control device 10 is in two sections, 22 and 24, which may be separated to permit access to the battery for purposes of the changing thereof. Sections 22 and 24 combine to provide a housing having generally flat bottom, side and end surfaces. The top surface, however, is stepped so that the end thereof which includes the socket 16 will fit within a receiver portion of the holder, the holder being indicated generally at 30.

The holder 30 is principally comprised of leather. Holder 30 includes a first element 32 which defines the opening into which the control unit 10 is received. Holder 30 also includes an electrode support element 34. Element 32 is comprised of a top portion 38, a pair of oppositely disposed side portions 40 and 42, a first end wall 44, a base portion 46, side walls 48 and 50, a second end wall 52, top portion 54 and additional side walls 56 and 58. The portions 46 and 54 and the walls 52, 56 and 58, define a holster or receiving pocket for the end of control device 10 which has the smaller cross-sectional area.

As indicated in FIG. 1, the side portions 40 and 42 are hinged to the top portion 38 by forming grooves in the leather. Strips of "Velcro" having the same characteristics, i.e., either hooks or eyes, are adhesively secured to the inside of side portions 40 and 42 as indicated at 60. The top portion 38 is hinged to the first end wall 44 which, in turn, is hinged to the base portion 46. The side walls 48 and 50 are folded up from base portion 46 and include, on outer surface areas thereof, "Velcro" fastener strips 62 which cooperate with the strips 60, i.e., the strips 62 are of the complementary type when compared to strips 60. If deemed necessary or desirable, additional short leather strips, as indicated at 64, may be adhesively secured to the outside of walls 48 and 50 to provide reinforcing. The end wall 52 is folded upwardly from base portion 46 and the top portion 54 is folded inwardly from top portion 54 and adhesively secured to the ends of respective side walls 48 and 50 to form the receptacle or holster.

The electrode support element 34 is comprised of a suitable non-conductive material and is generally L-shaped. Element 34 thus includes a plate or "flap" 66 which extends upwardly and is adhesively secured to the exterior of end wall 52. Element 34 is adhesively secured or otherwise suitably affixed to base portion 46. A plug supporting rectangular plate 70, comprised of a suitable non-conductive material, is adhesively secured to the inside of end wall 52 in the disclosed embodiment. If support element 34 is comprised of a plastic having the requisite rigidity, the "flap" 66 thereof can be drilled and tapped to receive the plug 72 and plate 70 can be eliminated. To facilitate assembly and enhance the asthetics of the product, if element 34 is comprised of plastic it will be positioned internally of element 32 rather than externally thereof as shown.

Plate 70, and the plug 72 which extends therefrom, may be clearly seen from FIG. 3. Plug 72 is affixed to plate 70 by means of sandwiching plate 70 between a pair of nuts which engage the threaded exterior housing portion of plug 72. The two conductors 84 and 86 which extend from plug 72 are directed to the region between electrode support element 34 and base portion 46 and extend therealong to make contact with respective of electrodes 80 and 82 (FIG. 2). These insulated conductors may be routed between plate 70 and end wall 52 and subsequently through an aperture provided in base portion 46. Preferably, however, the conductors will be positioned in the space between wall 52 and "flap" 66 and in the space between element 34 and base portion 46. To accomplish the foregoing when element 34 is comprised of leather, and plate 70 is included, the conductors will extend through an aperture in wall 52.

The conductors 84 and 86 are indicated in phantom in FIG. 2.

The electrodes 80 and 82 are preferably of the "button" shape which may seen by joint consideration of FIGS. 2 and 3. The electrodes may be either of the same diameter or of different diameters as depicted in FIG. 2. In the disclosed embodiment the spacing between electrodes 80 and 82 has been selected to be consistent with equine therapy. The spacing will be selected as a function of the use for which the apparatus is intended. The electrodes 80 and 82 will be attached to element 34 by any suitable technique. When element 34 is comprised of plastic the electrodes will typically be attached by means of "pop" rivets which extend through base portion 46.

In use, a battery will be inserted in the control unit 10 and the control unit then inserted, in the manner depicted in FIG. 1, in holder 30. As the control unit is inserted in the holder, the plug 72 will be engaged in socket 16 thereby establishing an electrical circuit between the pulse generation circuitry and the electrodes 80 and 82. Once the control unit 10 has been inserted in housing 30, the end wall 44 is folded about its hinged connection with base portion 46 and top portion 38 is subsequently folded about its hinge connection with end wall 44. The side portions 40 and 42 are then folded downwardly to bring the fastening strips 60 into contact with the cooperating fastening strips 62 on side walls 48 and 50 to thereby lock the control unit 10 within housing 30. The apparatus may then be used in the appropriate manner by manipulation of the controls 12 and 14 which are accessible through the open portion of the top of housing 30. Removal of control unit 10 from housing 30 is rapidly and easily accomplished merely by disengaging strips 60 from strips 62 and opening the housing to the condition shown in FIG. 1.

While a preferred embodiment has been shown and described, various modifications and substitutions may be made thereto without departing from the spirit and scope of the invention. Accordingly, it is to be understood that the present invention has been described by way of illustration and not limitation.

What is claimed is:

1. Electrotherapy apparatus comprising:

signal generator means, said signal generator means including a housing with first and second ends, a signal generator for providing output voltage pulses being disposed in said housing, said signal generator means further including an integral socket in said first end of said housing, said socket having at least a pair of electrical contacts, said signal generator being electrically connected to said contacts whereby output voltage pulses provided by said signal generator will be applied across said socket contacts; and case means for receiving and supporting said signal generator means, said case means including:

a receptacle defining member, said receptacle defining member being adjustable between an open signal generator means receiving condition and a closed signal generator means retention condition, said receptacle defining member being comprised of a non-conductive material and having a first substantially continuous flat side, said receptacle defining member further having a first pair of oppositely disposed walls extending in the same direction from opposite edges of said first side, said receptacle defining member additionally having a first end defining member articulated to said first side at one end thereof and a first top member articulated to said first end defining member, said receptacle defining member also having a second pair of oppositely disposed walls articulated to said top member, said receptacle defining member additionally including complementary fastener means on said walls of said first and second pairs of oppositely disposed walls, said fastener means cooperating such that said walls of said second pair may be releasably coupled to said walls of said first pair to define a receptacle wherein said first flat side is disposed opposite to and displaced from said top member;

a generally L-shaped electrode support member, said electrode support member including a base portion and a leg portion extending generally transversely with respect to said base portion, said electrode support member base portion being secured in abutting relationship to said receptacle defining member first flat side, said electrode support member leg portion extending at least part way across the receptacle defined by said receptacle defining member at the second end thereof, said second end being opposite to the end defined by said first end defining member;

a pair of electrodes mounted from said electrode support member base portion, said electrodes being spacially displaced and being positioned on the exterior surface of said case means;

a plug having at least a pair of electrically isolated contacts, said plug being complementary in shape to said signal generator means integral socket;

mounting means for said plug, said mounting means supporting said plug so that said plug projects into said case means defined receptacle at the second end thereof, insertion of said signal generator means into said case means causing engagement of said plug with said socket to establish electrical contact between respective contacts of said plug and socket; and conductors connected to and extending between individual of said electrodes and respective contacts of said plug contacts, said conductors being partly disposed between said electrode support member base portion and said receptacle defining member first flat side.

2. The apparatus of claim 1 wherein said fastener means are affixed to facing surfaces of said first and second pairs of walls, said fastener means cooperating to selectively open or close the end of said case means disposed oppositely to said receptacle second end.

3. The apparatus of claim 2 wherein said receptacle defining member further comprises a second end defining member extending from said first side, said second end defining member being generally transversely oriented with respect to said first side and joining said first side at the end thereof disposed oppositely with respect to said first end defining member, a second top member which extends from said second end defining member toward said first top member, and a further pair of wall members which extend transversely from said second top member, said further pair of wall members being affixed to said first pair of wall members, said second end defining member and second top member cooperating with said first side and said further pair of wall members to define an open-ended pocket to receive said signal generator means, said plug extending into said pocket.

4. The apparatus of claim 3 wherein an opening is formed between said first and second top members and wherein said signal generator means includes control elements, said control elements being accessible through said opening.

* * * * *